United States Patent [19]

Spivack et al.

[11] Patent Number: 4,605,692
[45] Date of Patent: Aug. 12, 1986

[54] SUBSTITUTED DIBENZO DIOXAPHOSPHEPINS AND DIOXAPHOSPHOCINS AS STABILIZERS

[75] Inventors: John D. Spivack, Spring Valley; Ramanathan Ravichandran, Yonkers, both of N.Y.

[73] Assignee: Ciba-Geigy Corporation, Ardsley, N.Y.

[21] Appl. No.: 682,648

[22] Filed: Dec. 17, 1984

[51] Int. Cl.$^4$ .............................................. C07F 9/15
[52] U.S. Cl. ..................................... 524/117; 558/85
[58] Field of Search ...................... 260/936; 524/117

[56] References Cited
U.S. PATENT DOCUMENTS
4,288,391 9/1981 Spivack ........................... 260/936

Primary Examiner—Anton H. Sutto
Attorney, Agent, or Firm—Harry Falber

[57] ABSTRACT

Hydroxyphenylthio-substituted phosphites of the formula

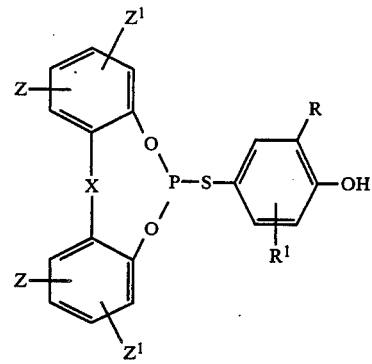

prepared by the reaction of the appropriate phosphorus and phenol compounds, said phosphites being useful as stabilizers of organic polymers and lubricating oils to counteract the degradative effects of light, heat and air.

13 Claims, No Drawings

SUBSTITUTED DIBENZO DIOXAPHOSPHEPINS AND DIOXAPHOSPHOCINS AS STABILIZERS

Organic polymeric materials such as plastics and resins and lubricating and mineral oils are subject to thermal, oxidative and photodegradation. A great variety of stabilizers are known in the art for stabilizing various substrates. Their effectiveness varies depending on the causes of degradation and the substrate stabilized. During the course of this work it was discovered that stabilizers that are very effective long term antioxidants are relatively poor process stabilizers which require stabilization of the substrate, against thermal degradation for a short time but at a relatively high temperature. Many stabilizers are relatively incompatible with the substrates which causes problems during the life of a product and lessens the stabilizer's effectiveness. Some stabilizers are either too volatile or thermally or hydrolytically unstable to be practical as commercial stabilizers.

The phosphites of this invention possess an unusual combination of desirable properties as compared to the prior art phosphites which makes these compounds particularly effective and useful as stabilizers. The prior art discloses unhindered 2,2'-biphenylenephenylphosphites and 2,2'-methylene bis-(dialkylphenyl)-phenylphosphites (Chem. Abst. 68, 12597Q (1968), Chem. Abst. 73, 15657A (1970), Chem. Abst. 75, 130242Q (1971) and Soviet Union Pat. Nos. 378,389, 429,070 and 440,390. In addition, alkanolamine phosphites are disclosed in U.S. Pat. Nos. 2,841,607 and 4,318,845. U.S. Pat. No. 3,852,395 discloses tris-(3,5-di-tert. -butyl-4-hydroxyphenylthio)phosphine. These compounds are all indicated to be stabilizers of various polymers.

The chemical literature also describes the reaction of an alkyl mercaptan with phosphorochloridites in the presence of a tertiary amine acid scavenger [J. Het. Chem. 20, 1311 (1983)]. U.S. Pat. No. 4,196,117 describes a similar reaction with a thiol to prepare various alkylated 1,1'-biphenyl-2,2'-diyl phosphites having thiosubstituents. These phosphites are distinct in structure from the instant compounds. In addition, they are more effective especially as process stabilizers for polyolefins and other substrates, both in preventing polymer chain scission as well as discoloration during high temperature processing.

Accordingly, it is the primary object of this invention to provide biphenyl cyclic phosphite compounds which exhibit improved process stabilization performance as contrasted with previously known phosphite compounds.

Various other objects and advantages of this invention will become evident from the following description thereof.

The compounds of this invention correspond to the formula:

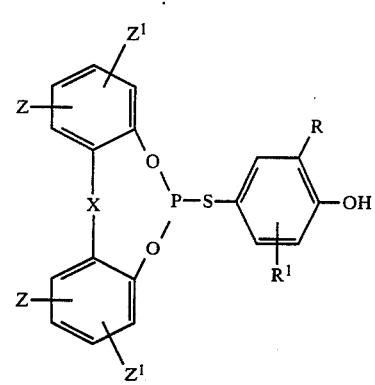

wherein

R and $R^1$ independently are hydrogen, alkyl of 1 to 18 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 12 carbon atoms;

Z and $Z^1$ independently are hydrogen, alkyl of 1 to 18 carbon atoms, cycloalkyl of 5 to 6 carbon atoms, phenyl or phenyl substituted by alkyl of 1 to 18 carbon atoms; and X is a direct bond, sulfur or alkylidene of 1 to 12 carbon atoms.

Preferred compounds within the above structure are those wherein Z or $Z^1$ are in ortho position to the phosphite oxygen in each of the phenyl groups.

The R, $R^1$, Z and $Z^1$ groups are preferably straight-chain or branched alkyl with 4 to 8 carbon atoms, such as n-butyl, sec-butyl, tert-butyl, tert-pentyl, 2-ethylhexyl, n-octyl and tert-octyl. The groups tert-butyl, tert-pentyl and tert-octyl are especially preferred. Also especially preferred is for the $R^1$ group to be in the ortho position to the hydroxyl group, particularly if $F^1$ is tert-alkyl.

Although $R^1$ can be hydrogen or alkyl of 1 to 18 carbons, preferably it is an alkyl group of 1 to 8 carbon atoms, either straight-chain or branched-chain. Especially preferred is tert-alkyl of 4 to 8 carbon atoms.

When the R and $R^1$ groups are aralkyl, they represent benzyl, α-methylbenzyl or α,α-dimethylbenzyl. Substituted phenyl can be for example tolyl, mesityl or xylyl.

X is preferably a direct bond or lower alkylidene of the formula

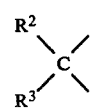

wherein $R^2$ and $R^3$ are independently hydrogen, phenyl or alkyl of 1 to 7 carbon atoms, provided that the number of carbon atoms does not exceed 12.

The phosphites of this invention can be prepared by reacting an alkylated 2,2'-bis-phenol or an alkylated 2,2'-alkylidene or thio-bis-phenol with phosphorus trichloride in a solvent to give the corresponding phosphorochloridite which in turn is reacted with an alkali metal alcoholate or phenolate to yield the desired product. The solvent is preferably aromatic, such as benzene, toluene, xylene and the like. A reaction temperature from room temperature to the reflux temperature of the reaction medium is generally utilized.

Another method for preparing the compounds of this invention involves reacting the phosphorochlordite with an appropriate alcohol or phenol optionally in the presence of a proton acceptor such as a tertiary amine, for example, triethylamine or pyridine.

The starting materials needed to prepare these phosphites are items of commerce or can be prepared by known methods.

Compounds of this invention are effective in stabilizing organic materials such as plastics, polymers and resins in addition to mineral and synthetic fluids such as lubricating oils, circulating oils, etc.

Substrates in which the compounds of this invention are particularly useful are polyolefins such as polyethylene and polpropylene; polystyrene, including especially impact polystyrene; ABS resin; elastomers such as e.g. butadiene rubber, EPM, EPDM, SBR and nitrile rubber.

In general polymers which can be stabilized include:

1. Polymers of monoolefins and diolefins, for example polyethylene (which optionally can be crosslinked), polypropylene, polyisobutylene, polybutene-1, polymethyl-pentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8 with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxy resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures or synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. Antioxidants 1.1 Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-b 4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6tert.butyl-2-methylphenol)
1,1-bis-(5-tert.butyl-4-hydroxy-2-methylphenyl)-butane
2,6-di-(3-tert. butyl-5-methyl-2-hydroxybenzyl)-4-methylphenol
1,1,3-tris-(5-tert.butyl-4-hydroxy-2-methylphenyl)-butane
1,1-bis:(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3-tert.butyl-2'-hydroxy-5'-methyl-benzyl)-6-tert.butyl-4-methylphenyl]-terephthalate.

1.5. Benzyl compounds, for example,
1,3,5-tri-(3,5-di-tert.butyl-4-hydroxybenzyl)-2,4,6-trimethylbenzene-di-(3,5-di-tert.butyl-4-hydroxybenzyl)sulfide
3,5di-tert.butyl-4-hydroxybenzyl-mercapto-acetic acid isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbaminate 1.7. Esters of β-(3,5-di-tert.butyl-4-hydroxyphenyl)propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of β-(5-tert.butyl-4-hydroxy-3-methylphenyl)-propionic acid with monohydric or polyhydric alcohols, for example,

| | |
|---|---|
| methanol | diethyleneglycol |
| octadecanol | triethyleneglycol |
| 1,6-hexanediol | pentaerytritol |
| neopentylglycol | tris-hydroxyethyl isocyanurate |
| thiodiethyleneglycol | di-hydroxyethyl oxalic acid diamide |

1.9. Amides of β-(3,5-di-tert.butyl:4-hydroxyphenyl)-propionic acid for example, N,N'-di-(3,5-di-tert.butyl-4-hydroxyphenylpropionyl)-hexamethylendiamine N,N'-di-(3,5-di-tert.butyl-4-hydroxyphenylpropionyl)-trimethylendiamine N,N'-di-(3,5-di-tert.butyl-4-hydroxyphenylpropionyl)-hydraxine 2. UV absorbers and light stabilizers 2.1. 2-(2'-Hydroxyphenyl)-benztriazoles, for example, the 5'-methyl-, 3',5'-di-tert.butyl-, 5'-tert.butyl, 5'-(1,1,3,3-tetramethylbutyl)-, 5-chloro-3',5'-di-tert.butyl-, 5-chloro-3'-tert.butyl-5'-methyl-, 3'-sec.butyl-5'tert.butyl-, 4'-octoxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4dodecyloxy-, 4-benzyloxy, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis:(4-tert.butylbenzoyl)-resorcinol, benzoylresorcinol, 3,5-di-tert.butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methylindoline.

2.5. Nickel compounds, for example, nickel complexes of 2,2'-thio-bis-[4-(1,1,3,3-tertramethylbutyl0-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example
bis-(2,2,6,6-tetramethylpiperidyl)-sebacate
bis-(1,2,2,6,6-pentamethylpiperidyl)-sebacate
n-butyl-3,5-di-tert.butyl-4-hydroxybenzyl malonic acid
bis-(1,2,2,6,6-pentamethylpiperidyl)ester, condensation product of 1-hydroxyethyl-2,2,6,6-tetramethyl-4hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris(2,2,6,6tetramethylpiperidyl)-nitrilotriacetate, tetrakis-(2,2,6,6-tetramethyl-4piperidyl)-1,2,3,4-butanetetracarbonic acid, 1,1' (1,2-ethanediyl)-bis-(3,3,5,5-tetramethylpiperazinone).

2.7. Oxalic acid diamides, for example, 4,4'-di-octyloxyoxanilide, 2,2'-di-octyloxy-5,5'-di-tert.butyl-oxanilide, 2,2'-di-dodecyloxy-5,5'-di-tert.butyl-oxanilide, 2-ethoxy2'-ethyl-oxanilide, N,N'-bis (3dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-.butyl-4-hydroxyphenylpropionyl)-hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaery-thritol diphosphite, tris-(2,4-di-tert.butylphenyl) phosphite, di-isodecylpentaerythritol diphosphite, di-(2,4-ditert.butylphenyl)pentaerythritol diphosphite, tristearyl-sorbite triphosphite, tetrakis-(2,4-di-tert.butylphenyl)-4,4'-diphenylylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for eample, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

2,4,8,10-Tetra-tert-butyl-6-[3,5-di-tert-butyl-4-hydroxyphenylthio]-12H-dibenzo [d,g] [1,3,2] dioxaphosphocin.

In a flame dried flask under nitrogen, 6.87 grams of phosphorous trichloride in 100 ml of dry toluene was treated with a solution of 21.27 grams of 2,2'-methylenebis-(4,6-di-tert-butylphenol) and 10.12 grams of triethylamine in 80 ml of dry toluene at a temperature not exceeding 5° C. The reaction was stirred at ambient temperature for eight hours and then cooled to 5° C. A solution of 11.92 grams of 2,6-di-tert-butyl-4mercaptophenyl and 5.1 grams of triethylamine was then added and the reaction mixture stirred at ambient temperature for a further eight hours. The mixture was filtered and the filtrate concentrated under reduced pressure. The residue was recrystallized from toluene/heptane to give a white crystalline product, m.p. 280°-82° C.

Analysis calculated for: $C_{43}H_{63}PO_3S$; C, 74.73; H, 9.21. Found: C, 75.0; H, 9.5.

EXAMPLE 2

2,4,8,10-Tetra-tert-butyl-6-[3,5-di-tert-butyl-4-hydroxyphenylthio]dibenzo [d,f] [1,3,2] dioxaphosphepin.

In a flame flask under nitrogen, 2.2 grams of phosphorous trichloride in 50 ml of dry toluene was treated with a solution of 10.27 grams of 3,3',5,5'-tetra-tertbutylbiphenyl-2',2'-diol and 6.79 ml of triethylamine in 40 ml of dry toluene at a temperature not exceeding 5° C. A solution of 5.96 grams of 2,6-di-tert-butyl-4-mercaptophenol and 3.48 ml of triethylamine in 10 ml of dry toluene was then added and the reaction mixture stirred at ambient temperature for a further 15 hours. The mixture was filtered and the filtrate concentrated under reduced pressure. The residue was chromatographed on silica gel with ethyl acetate:heptane (1:7) to give the product as a while foam.

Analysis calculated for: $C_{42}H_{61}O_3PS$; C, 74.51; H, 9.10. Found: C, 74.5; H, 9.4.

EXAMPLE 3

Processing Stability of Polypropylene Base Formulation

| Polypropylene* | 100 parts |
|---|---|
| Calcium Stearate | 0.10 parts |

*Profax 6501 from Himont, USA

Stabilizers were solvent blended into polypropylene as solutions in methylene chloride and, after removal of the solvent by evaporation at reduced pressure, the resin was extruded using the following extruder conditions:

Temperature (°C.)

| Cylinder #1 | 232 |
|---|---|
| Cylinder #2 | 246 |
| Cylinder #3 | 260 |
| Die #1 | 260 |
| Die #2 | 260 |
| Die #3 | 260 |
| RPM | 100 |

During extrusion, the internal extruxder pressure was determined using a pressure transducer. After each of the first, third and fifth extrusions, resin pellets were compression molded into 125 mil (3.2 mm) thick plaques at 193° C. and specimen yellowness index (Y.I.) determined according to ASTM D1925-63T. The results are tabulated in the following table:

Extrusion Temperature—260° C.

| Additives | Transducer Pressure After Extrusion (psig) | | | YI Color After Extrusion | | |
|---|---|---|---|---|---|---|
| | 1 | 3 | 5 | 1 | 3 | 5 |
| None | 615 | 570 | 510 | 4.3 | 6.1 | 7.4 |
| 0.1% Ex. 1 | 780 | 735 | 700 | 8.0 | 10.9 | 11.3 |
| 0.1% Ex. 2 | 720 | 705 | 670 | 3.5 | 7.6 | 8.3 |
| 0.1% Antioxidant A* | 690 | 675 | 630 | 7.2 | 11.7 | 15.3 |

*Neopentyltetrayl tetrakis[3-(3',5'-di-tert.butyl-4'-hydroxyphenyl)propanoate]

These data evidence the effective processing stability provided by the compounds of this invention.

EXAMPLE 4

Unstabilized polypropylene powder (Hercules Profax 6501) was thoroughly blended with the indicated amount of additive. The blended materials were then milled on a two roll mill at 182° C. for 5 minutes, after which time the stabilized polypropylene was sheeted from the mill and allowed to cool. The milled polypropylene was then cut into pieces and compression molded on a hydraulic press at 220° C. and 175 psi ($1.2 \times 10^6$ Pa) into 25 mil thick plaques. The sample was exposed in a fluorescent sunlight/black light chamber until failure. Failure is taken as the hours required to reach 0.5 carbonyl absorbance by infrared spectroscopy on the exposed films.

| Additive Compound of | Additive Conc. (% by weight) | FS/BL Test Results (Hours to Failure) |
|---|---|---|
| None | — | 100 |
| Example 1 | 0.2 | 400 |
| Example 2 | 0.2 | 360 |

These data further indicate the effective stabilization activity of the instant compounds.

Summarizing, it is seen that this invention provides novel cyclic phosphite compounds which exhibit effective stabilization activity. Variations may be made in proportions, procedures and materials without departing from the scope of the invention as defined by the following claims.

What is claimed is:

1. A compound of the formula

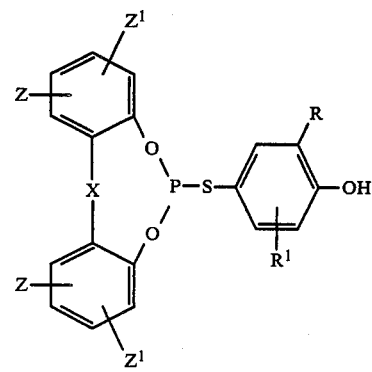

wherein
R and $R^1$ independently are hydrogen, alkyl of 1 to 18 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 12 carbon atoms;

Z and $Z^1$ independently are hydrogen, alkyl of 1 to 18 carbon atoms, cycloalkyl of 5 to 6 carbon atoms, phenyl or phenyl substituted by alkyl of 1 to 18 carbon atoms; and X is a direct bond, sulfur or alkylidene of 1 to 12 carbon atoms.

2. The compound of claim 1, wherein Z or $Z^1$ are in the ortho position to the phosphite oxygen in each of the phenyl rings.

3. The compound of claim 1, wherein $R^1$ is in the ortho position to the hydroxyl group.

4. The compound of claim 1, wherein R, $R^1$, Z and $Z^1$ are alkyl of from 4 to 8 carbon atoms.

5. The compound of claim 4, where R, $R^1$, Z and $Z^1$ are tert.alkyl of from 4 to 8 carbon atoms.

6. The compound of claim 3, wherein R, $R^1$, Z and $Z^1$ are tert.butyl, tert.pentyl or tert.octyl.

7. The compound of claim 1, wherein X is a direct bond or alkylidene of the formula

wherein $R^2$ and $R^3$ are independently hydrogen, phenyl or alkyl of from 1 to 7 carbon atoms, provided that the total number of carbon atoms does not exceed 12.

8. 2,4,8,10-Tetra-tert-butyl-6-[3,5-di-tert-butyl-4-hydroxyphenylthio]-12H-dibenzo [d,g] [1,3,2] dioxaphosphocin, according to claim 1.

9. 2,4,8,10-Tetra-tert-butyl-6-[3,5-di-tert-butyl-4-hydroxyphenylthio]-dibenzo [d,f] [1,3,2] dioxaphosphepin, according to claim 1.

10. A composition of matter comprising an organic material subject to oxidative, thermal and actinic degradation stabilized with an effective stabilizing amount of a compound of claim 1.

11. The composition of claim 10, wherein the organic material is a synthetic polymer.

12. The composition of claim 11, wherein said polymer is selected from the group consisting of polyolefins, impact polystyrene, ABS resin, butadiene rubber, EPM, EPDM, SBR and nitrile rubber.

13. A method for stabilizing an organic material against oxidative, thermal and actinic degradation which comprises incorporating into said organic material an effective stabilizing amount of a compound of claim 1.

* * * * *